(12) United States Patent  (10) Patent No.: US 7,472,560 B2
Karch et al.  (45) Date of Patent: Jan. 6, 2009

(54) LIGHTWEIGHT NON-BULKY PERSONAL COOLING DEVICE

(75) Inventors: Jackie Shawn Karch, Chico, TX (US);
Diane Marie Karch, Chico, TX (US)

(73) Assignee: Diane Karch, Gainesville, TX (US)

( * ) Notice: Subject to any disclaimer, the term of this patent is extended or adjusted under 35 U.S.C. 154(b) by 487 days.

(21) Appl. No.: 11/182,902

(22) Filed: Jul. 18, 2005

(65) Prior Publication Data

US 2007/0028350 A1  Feb. 8, 2007

(51) Int. Cl.
*F25D 23/12* (2006.01)
(52) U.S. Cl. ...................................... 62/259.3
(58) Field of Classification Search ............... 62/259.3; 2/102, 458, 171.3
See application file for complete search history.

(56) References Cited

U.S. PATENT DOCUMENTS 3,291,126 A * 12/1966 Messick ................ 128/201.29

2004/0168459 A1 * 9/2004 Blackstone ................ 62/259.2
2005/0016199 A1 * 1/2005 Blackstone ................. 62/420

* cited by examiner

*Primary Examiner*—Melvin Jones
(74) *Attorney, Agent, or Firm*—Mary Helen Sears; M.H. Sears Law Firm Chartered

(57) ABSTRACT

A lightweight, non-bulky personal cooling device consists of a (1) first length of flexible tubing adapted to fit around the wearer's torso or another of the wearer's body parts, which tubing contains at least two perforations and desirably a series thereof that are situated to facilitate air cooling of the torso or other body part and connect at both ends to (2) a T or Y-shaped connector having an additional inlet to which is connected (3) a second length of flexible tubing which is unperforated and is in turn connected (4) to a hand operatable air aspirator member whereby air is drawn in through the second flexible tubing and through the T or Y connector to the first flexible tubing from which air exits to the skin of the wearer and cools it. The preferred air aspirator is a sphygmanometer which can be carried in a pocket, or in a pouch attached to the wearer.

7 Claims, 3 Drawing Sheets

LIGHTWEIGHT NON-BULKY PERSONAL COOLING DEVICE

The present invention relates to a simple device for air cooling selected human body portions, especially the torso, of persons who wear protective vests and/or other heavy protective clothing having a tendency to overheat parts of the human body.

BACKGROUND OF THE INVENTION

It has been recognized for sometime that persons, such as law enforcement officers and members of the armed forces and others whose work requires them at times to wear heavy protective clothing, e.g., bulletproof ("ballistic") vests, are prone to becoming seriously overheated and very uncomfortable, especially in those body areas covered by such clothing. This overheating results from the fact that the natural heat of the body is trapped inside heavy protective clothing and tends to accumulate, causing body temperature to rise and thereby triggering the body's own natural perspiration defense to such a condition. Unfortunately, with the protective clothing still in place, perspiration is unable to evaporate and thereby counter the overheating effect of the clothing. Because the ultimate effect of wearing heavy protective clothing over a period of many hours can lead to skin rashes and other skin eruptions or may even so affect the wearer overall as to cause other abnormal physical reactions such as temporary collapse, cardiac or pulmonary reactions, etc., a number of approaches have been developed to alleviating the severe overheating and discomfort that habitual wearers of heavy protective clothing normally experience.

Many of these approaches involve the creation of pockets or channels in the protective clothing for circulating coolants of some nature. Some examples may be found in: (1) U.S. Pat. No. 3,610,323 to Troyer wherein tubular networks in the garment carry cool water containing a refrigerant which is gradually heated by the wearer's body heat, and is then pumped out by a hand operated pump that the wearer controls, through capillary openings in the tubes and is replaced by fresh coolant liquid from an auxiliary source; and (2) U.S. Pat. No. 4,998,415 describes "body cooling" approaches comprising a vest and a headband each equipped with flexible tubes through which a liquid coolant is fed from an auxiliary pressurized container. As the wearer's body heat increases, the coolant vaporizes and is passed to an auxiliary compressor, followed by a condenser which reliquefies it and returns it to the auxiliary pressurized container. Meanwhile additional coolant from the container is pumped into the flexible tube system of the wearer's vest and head band, and the entire cycle is repeated over and over. This patent refers to a number of prior devices, including the Troyer U.S. Pat. No. 3,610,323 which operate generally on a principle of cycling liquid coolant through flexible tubing of a protective garment and discarding or recycling the coolant material when body heat has vaporized it, followed by circulating a fresh increment of coolant into the garment.

Other types of garments operating on similar principles, all requiring liquid or gas for replenishing are described in, e.g. U.S. Pat. No. 6,349,412 to Dean; U.S. Pat. No. 5,255,390 to Gross et al: U.S. Pat. No. 3,348,236 to Copeland, U.S. Pat. No. 5,201,365 to Siegel and U.S. Pat. No. 5,005,216 to Blackburn et al.

Still other known approaches involve garments that can be fitted with replaceable gel packs of coolants such as disclosed by Steele et al in U.S. Pat. Nos. 5,146,625 and 5,305,471 and by Colvin et al in U.S. Pat. No. 5,415,222. The latter discloses a garment which contains pouches containing encapsulated fluid comprising low melting paraffinic materials that are caused to liquefy by the wearer's body heat and are then replaced. The liquefied contents of the pouches may be allowed to resolidify and may be reused or discarded and, in either event, are replaced by fresh pouches of the same type. U.S. Pat. No. 5,524,293 to Kung shows a vest arranged to receive flexible cooled water or ice containing vessels, wherein the vessels must be replaced as the ice melts and warms or as the water warms.

U.S. Pat. No. 3,429,138 to Goldmerstein involves a separate interior vest equipped with, e.g., a sponge soaked with water or coolant. In this case, the vest itself is also soaked in water. Stuebner et al U.S. Pat. No. 4,580,408 shows a multilayer water saturated vest for motocross riders which cools the wearer at the water in each layer evaporates in successive stages. U.S. Pat. No. 5,755,110 discloses a vest with seamed partitions which contain beads of polyacrylamide or another absorbent for water or other coolant liquid. This vest has air intake openings in each seamed conduit and is equipped with one-way intake valves and one-way exhaust valves operable by the wearer's respiration which act alternately to draw more air in and exhaust warmed air. The beads may be re-wetted by soaking the garment in the coolant medium. Frank et al U.S. Pat. No. 6,128,784 also discloses a self-ventilating vest operated by the wearer's respiration which allows both intake of air and exhaustion of air.

While the foregoing are only a sampling of prior art garments which might substitute for or add to heavy protective garments and enable some cooling of the body of a person whose occupation requires the wearing of heavy protective clothing, it is clear that all have some disadvantages, even while providing some cooling effects.

Protective clothing is in itself extremely cumbersome and heavy. Modifications that require the wearer to be burdened with an auxiliary container that is a source of coolant medium are often totally impractical. If essentially stationary, they restrict the protective clothing wearer's freedom of movement. If portable, they represent an added burden upon a person who may also be laden with other heavy gear, such as firearms, ammunition, flashlights, handcuffs, radio equipment, etc.

Garments equipped with replaceable gel packs, coolant cartridges, etc., represent an additional inconvenience to the wearer in that he or she must ensure that replacements are readily available when needed. In addition, these accoutrements add to the weight of the garment and may increase wearer discomfort in the same way that the need to carry a pressurized tank of coolant material does.

To the extent some of the cited prior art requires an extra internal garment for cooling that must be re-wetted from time to time or a self-ventilating garment is burdened with extra weight by reason of including flexible tubes, intake and exhaust valves, etc. problems may constantly arise due to inadvertent punctures, jamming of valves and other mishaps. All of these added concerns to which the wearer must be alert are an added burden upon the minds of personnel whose jobs are often fraught with external danger of a serious nature requiring them to exercise intense alertness and to have minimal mental distraction.

It is an object of this invention to provide a lightweight self-operable apparatus that can easily be worn in addition to a protective vest or other heavy and often cumbersome clothing.

Another object is to provide air cooling of the body which the wearer can be easily direct to spots at which it is most needed.

Still another object is to provide a simple and easily operatable cooling method requiring no extraneous pressuring tanks, coolant packs or other paraphernalia, which cooling method is operatable in any environment and virtually at any time, at the option of the wearer.

BRIEF DESCRIPTION OF THE INVENTION

The device of the present invention consists of a simple flexible cooling tube, normally approximately 4 to 6 feet long, depending upon the girth of the intended wearer, which is attached at both of its ends to a single "T" or "Y" shaped connector, thus forming a loop that can be worn around the torso inside heavy protective clothing. Preferably when the protective clothing is a vest, the device of this invention is constructed so that it rests on one of this tube wearer's shoulders and is looped under the opposite arm, while the "T" or "Y" shaped member rests at or slightly above the wearer's waist. At least two small diameter holes of a few centimeters each must be made in the tubing at points roughly at the center of the wearer's back, but any number of such holes can be added around the periphery of the wearer's body to ensure maximum cooling and comfort.

A second length of the same flexible tubing is connected to the third inlet of the "T" or "Y" connector and to a common air aspirator such as a sphygmanometer having a rubber bulb readily operatable by a human hand. This length of tubing is often considerably shorter than the first one, often as short as 8-12 inches in length, but it may be made longer or shorter so as to ensure that the air aspirator is readily accessible to one of the wearer's hands. In the case of a device intended to be worn by a law enforcement officer, for example, the device may be so fashioned that the air aspirator bulb rests inside a lightweight nylon or other cloth carrying case which buttons, snaps, closes with Velcro or otherwise attaches over the wearer's belt, so that the bulb of the aspirator can be operated by merely squeezing the carrying case. It is also foreseeable that the aspirator might be rested in a pocket located near the wearer's waist or in a uniform breast pocket. Of course the shorter piece of tubing can also be adjusted to be accessible to the individual wearer in any other position that wearer find as most comfortable and easiest to access. Various other placements of the aspirator in relation to the long body-encircling tube are also obviously possible.

While described mainly as a device to cool the front and back of the torso, it is important that this device, wherein the air aspirator, operated by the wearer as needed, simply pumps air into the area between the heavy protective clothing, wherever worn on the body and the wearer's skin, can be modified in length of both pieces of flexible tubing, in number of holes in the tubing which carries air into the wearer's skin and in all other respects, to cool one or both of the wearer's arms or legs or e.g., the back and front of the wearer's neck.

DETAILED DESCRIPTION OF THE INVENTION

Figure 1:
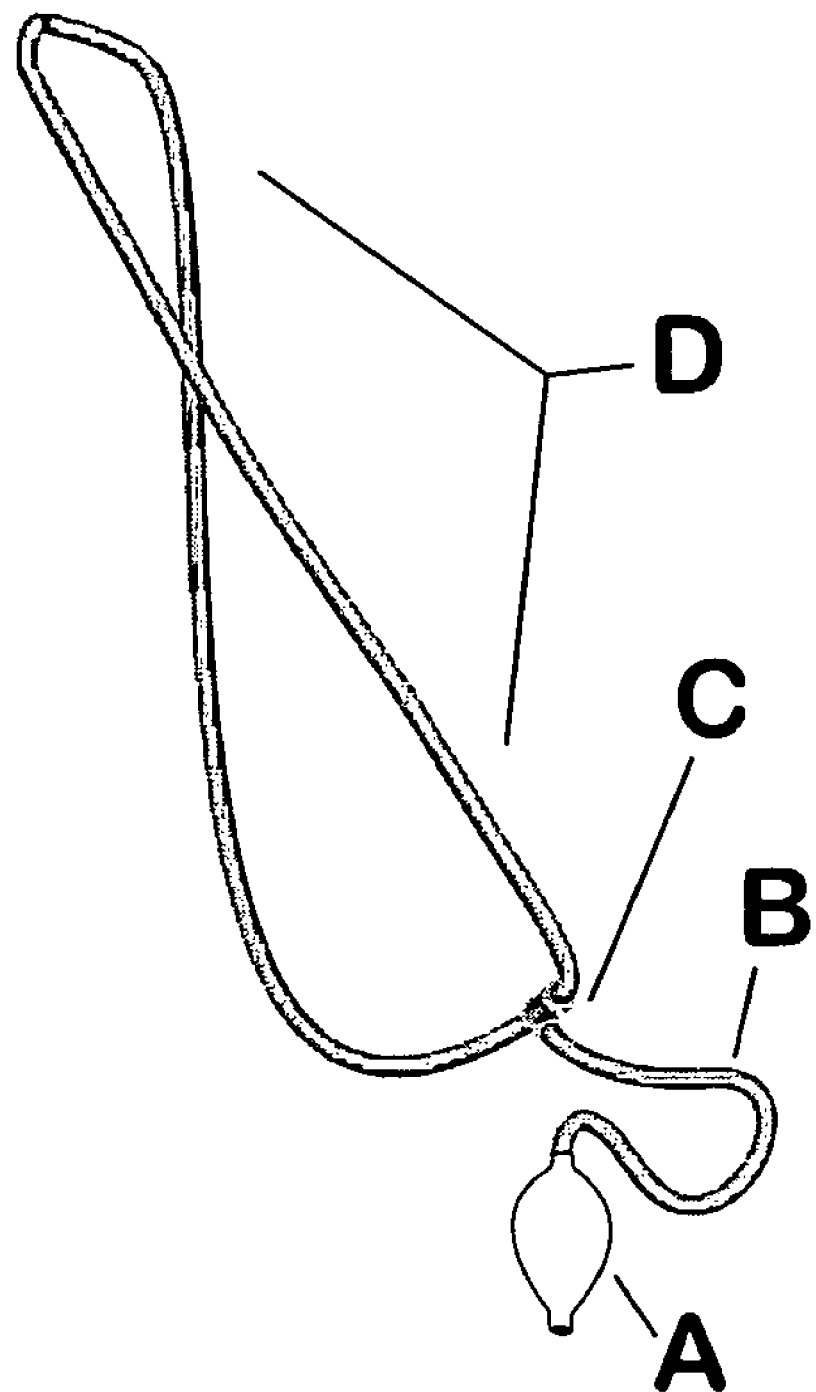
FIG. 1 hereof is a drawing of an exemplary device of this invention.

The personal cooling tube device of this invention was particularly inspired by intimate knowledge of the special needs of law enforcement officers relative to cooling, under circumstances where they are required to wear heavy ballistics vests in hot weather. These vests, in general, are often made from multiple layers, in the order of up to 13 layers of the plastic Kevlar®, an excellent insulator especially when multilayered, that is particularly uncomfortable to wear in any warm environment.

The use, of the device of this invention however, is in no sense limited to law enforcement personnel or even to personnel that are required wear ballistic vests. Many other people who wear protective clothing, especially under very warm ambient conditions, can benefit from the device of this invention. Members of the armed forces, firefighters, players of various sports, especially professionals who train and often play under extremely warm weather conditions, construction workers, amusement park personnel and their patrons, and anyone else who must work under extremely warm conditions or who must wear protective heavy clothing in warm weather can benefit from wearing this simple, efficient, lightweight, non-obstructive device.

The longer tube, sometimes referred to as the "upper tube" and the shorter tube, sometimes called "the lower tube" are both preferably made from clear vinyl tubing material, but any type of flexible plastic tubing, such as polypropylene, nylon, silicone-based plastic, high density polyethylene, or even latex could be used. It has been found that almost any flexible tubing of a diametric size such that it is not uncomfortable to wear on the human skin is acceptable. Of course, care should be taken, for example, with latex or any other material which is known to cause allergenic skin reactions in some persons. It has been found that a particularly useful plastic tubing that is readily available has an outer diameter of approximately ¼ inch and an inner diameter of about ⅛ inch, but the size of the tubing is not critical and it is only necessary that the tubing be able to supply air to the skin through the perforations in the "longer" tube and that the "shorter" tube carry air to the "longer" tube and, further that no tubing be so heavy or thick as to be uncomfortable for the wearer.

As already noted the longer tube which is intended to provide the cooling effect should have at least two perforations or holes, so as to cool both sides(front and back) of the wearer, but any number of holes may be made to ensure proper ventilation to the body or body part that the wearer wishes to cool. These holes may be drilled into the tubing or they may be made by any other acceptable mechanical means. The holes may be round, square, or of any other convenient shape. In some instances it may be desirable, for most efficient cooling, to establish a series of holes of different sizes at intervals along the portion of the tube that contacts the human body.

The "T" or "Y" shaped connector is a commonly available plastic item which is used in this devise to connect the continuous unperforated plastic piping that connects to the air aspirator (the "shorter" or "upper" tube) to the longer or "lower") perforated tube. Because this longer tube is connected to the "T" or "Y" at both of its ends, air can flow through the perforations in the tube in both directions around the wearer's body or the body part to be cooled. Because the amount of air conveyed to the body is not excessive, no need exists for any type of special exhaust means; the gentle circulation set up by the device in combination with the natural tendency of air to exhaust through pores in clothing and other small openings around armholes, neck and the like, is enough to exhaust air that has warmed and permit the entry of cooler air as long as the device is being operated. In place of the "T" or "Y" shaped connector, other types of connectors having the same function could be substituted. In particular an "X" connector, of a type commonly available, can be readily made suitable by blocking one of its inlets. Alternatively, its four inlets can be rendered useful by attaching each of the two left free when the so-called "upper" or "longer" tube is attached thereto to a shorter (or "lower") tube each free end of which is itself attached to a separate air aspirator, thereby enabling additional air to be pumped to the wearer's body.

While the "shorter" or "lower" tube is typically 8 to 12 inches in length while the "longer" or "upper" is most often between about 4 and about 6 feet long, at least when the device is intended that either or both tubes may be of any length that is convenient for the size of person who is to wear the device or for the body part specifically desired to be cooled. In particular, adaptations of the device sized for cooling, e.g., an arm, a leg or the human neck may require that the tube appended to the air aspirator be longer that the one intended to cool the body part by delivering air to it. Similarly, a device adapted to cool a leg may have a shorter perforated tube and a longer unperforated tube in order to allow the wearer easily to access the air aspirator with one hand. Any number of variations for particular purposes will readily occur to people in various specialized occupations who might benefit from being able to cool a particular part of the human body with the simple, non-obstructive lightweight device of this invention, and all such modifications and variations are intended to be comprehended herein.

The air aspirator particularly preferred to be used in the device of this invention is a common rubber bulb aspirator known as a sphygmanometer, of the type used with blood pressure measuring apparatus. It is approximately 3.25 inches long and about 1.5 inches wide at its widest point. Such a device is easily fitted into a pocket or into a small cloth pouch that can be fastened to the device wearer's belt. Another convenient way of attaching the aspirator to the wearer involves making a small buttonhole or other opening that is otherwise stabilized with binding material or by hemstitching or by any other technique used to create a stable opening in fabric, in the wearer's outer shirt. The tube attaching the air aspirator to the "T" or "Y" connector can then be threaded— through this opening thus leaving the wearer able to reach the squeezable rubber bulb of the aspirator readily whenever air cooling is desired, but locating the aspirator in an unobtrusive place where it is unlikely to disturb the wearer or be disturbed under normal conditions.

As will readily be recognized, many other forms of air aspirator could be used, including bicycle tire pumps, various types of air pumps and air compressors including miniature and electronic air compressors, mini-pumps, etc. The sphygmanometer type of aspirator is preferred for its light weight and consequent ready portability and for its ease of hand operation.

In the testing of the device of this invention by a human subject who wears a ballistic vest daily, it was noticed that at times, especially when the skin is perspiring profusely, the first length of tubing may stick to the skin, causing at least some of multiple perforations through which air flows to the skin in the tubing at back or front, or both, to become blocked or clogged, so that air cooling stops in the region where this occurs. To alleviate this problem at both back and front of a torso cooling device, it was found effective to seat in at least one of a plurality of perforations at both the wearer's back and front a small "T" or "Y" shaped connector having an inner diameter in its twin branched inlets not more than about ½ that of the inner diameter of the flexible tubing. This small connector can easily be positioned against the skin so that it primarily acts as a spacer of the skin from the adjacent portions of the first length of tubing. The effect is to break any moisture seal caused by adherence of one or more perforations situated in adjoining portions of the tubing to the skin surface, facilitate evaporation of moisture blocking these perforations of the tubing and thereby enable perforations in the tubing to resume rapid delivery of cooling air to the skin.

This modification of the device involving the inclusion of tiny "T" or "Y" "spacers" at required intervals along the periphery of the first length of tubing, is particularly useful in cooling devices of this invention that are to be used by persons who tend to perspire heavily and whose protective clothing is particularly heavy. Many people, however, will find the unmodified device as earlier described adequate to their personal cooling needs. It is preferred to provide the device of this invention, when not in use on a human wearer's body with a lightweight pouch-type carrying case made of nylon or other lightweight fabric of the type in which law enforcement officers typically carry pepper spray. This type of case can readily be secured to a belt by placing its flap over the top of the officer's belt and snapping the flap to the part of the case that is behind and partially below the officer's belt. Any bag, pouch or case similarly capable of being fastened to a belt could be used for this purpose. It is to be understood that while this pouch enhances the convenience of the device of the invention for many wearers and provides a place within which the device can be stored when not needed, it is not an essential and has nothing directly to do with the functioning of the device. As noted earlier, however, it can conveniently hold the air aspirator portion of the device when the device itself is being used to cool the portions of the body covered by a ballistic vest. Moreover, since the pouch is soft and flexible, the wearer of the pouch containing the aspirator can activate the aspirator by simply squeezing the pouch.

In the appended drawings, FIG. 1 shows an assembled device of this invention wherein A denotes the air aspirating sphygmanometer, B is the so-called "lower" or shorter tube, C denotes a "T" connector D is the longer or "upper" tube designed to encircle the upper torso and cool the skin beneath a ballistic vest or similarly constructed heavy vest.

Figure 2:
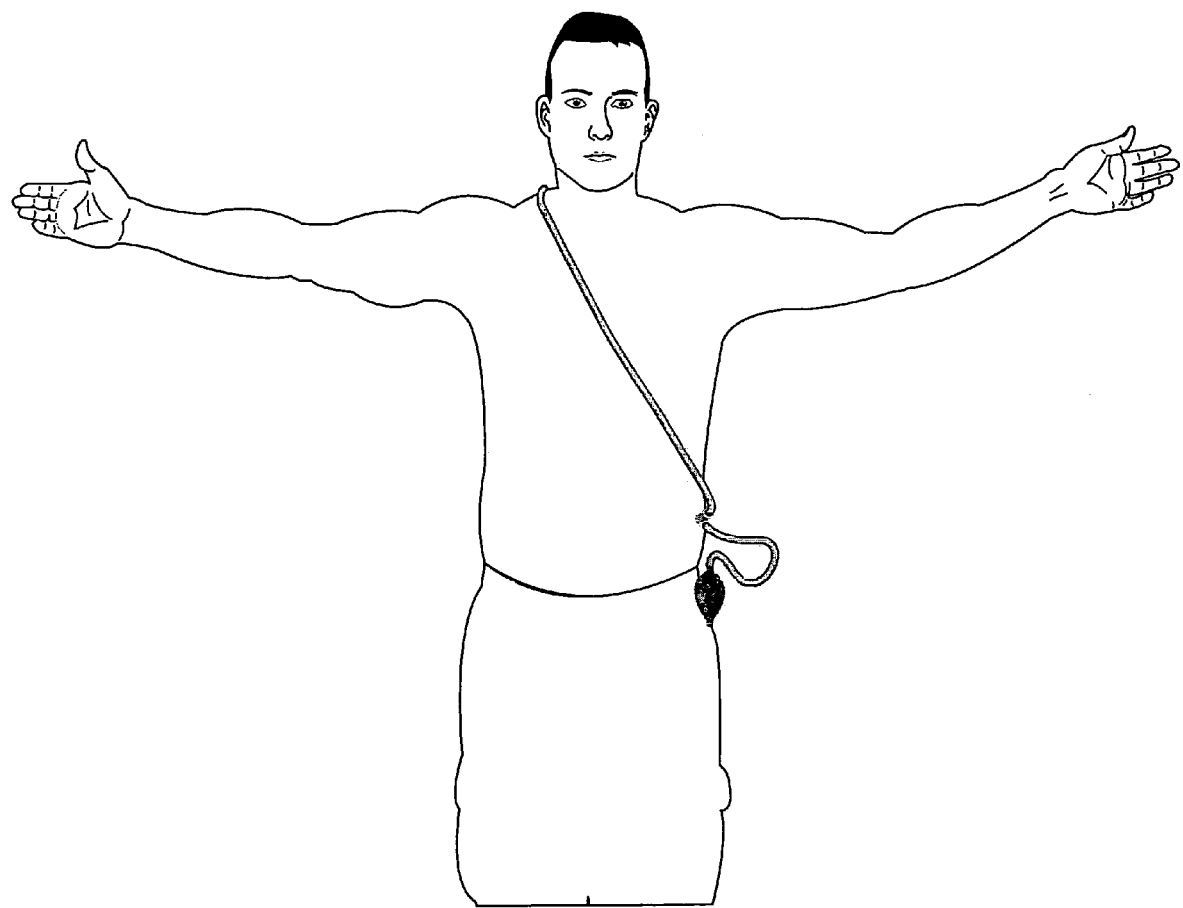
FIG. 2 is a sketch showing how the device might be worn on the torso of a person whose requires the wearing of a protective ballistic vest.
Figure 3:
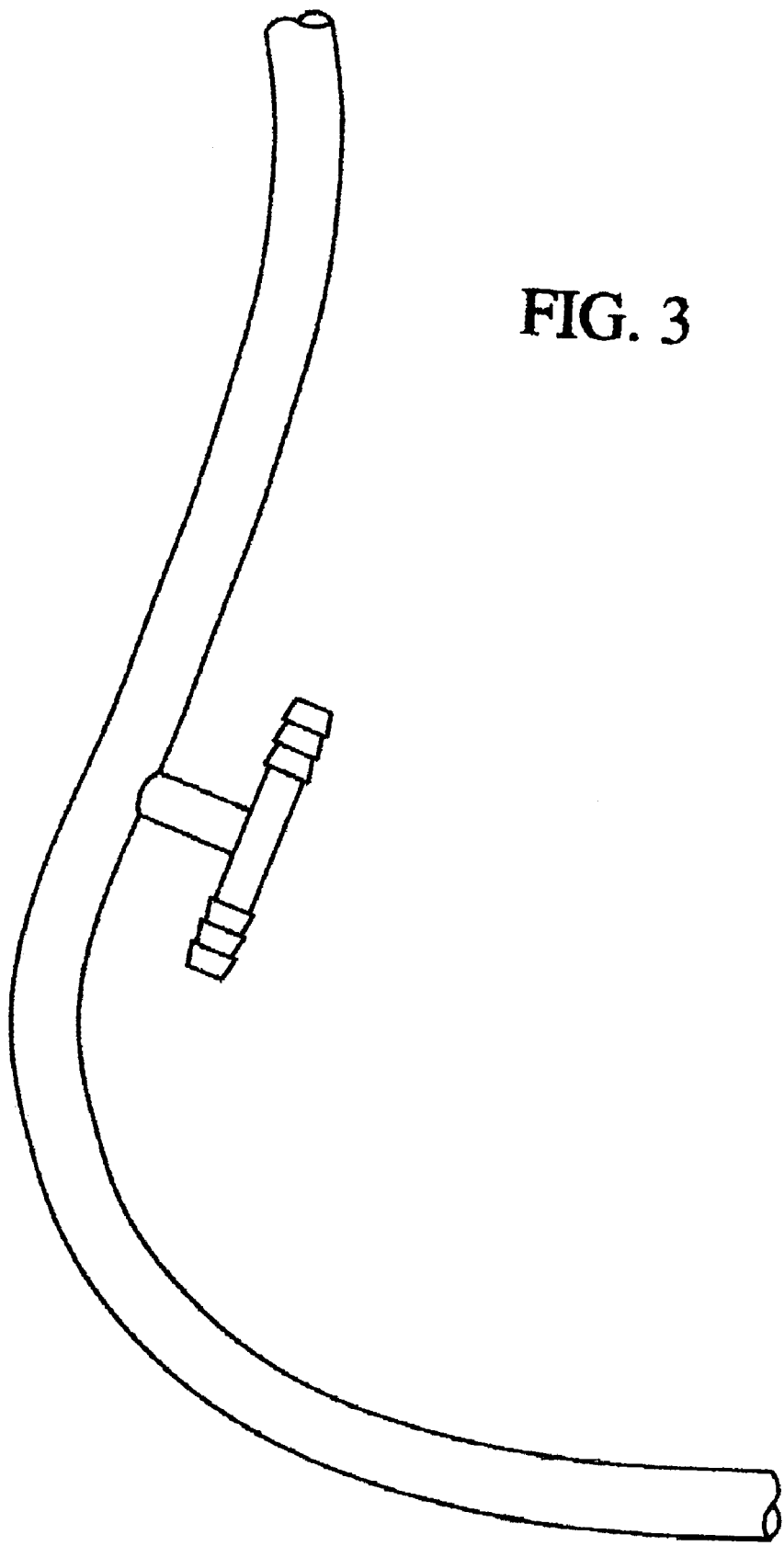
FIG. 3 illustrates the use of a small "T" or "Y" shaped connector having an inner diameter in its twin branched inlets not more than about ½ the inner diameter of the flexible tubing to act as a spacer of the wearer's skin from adjacent positions of the tubing.

FIG. 2 illustrates how the device of FIG. 1 is typically positioned on the skin of a law enforcement officer prior to his donning the ballistic vest. In FIG. 2, the "shorter" or "lower" tube is seen attached to third inlet of a T shaped connector and is so positioned that when the officer dons his outer his outer shirt, the tube appended to the air aspirator can be momentarily disconnected, threaded through a small well-stabilized buttonhole opening created in the shirt itself and then reconnected to the T connector, leaving the air aspirator bulb outside both the shirt and the ballistic vest beneath the shirt. The air aspirator is thus conveniently at hand to be squeezed and thus pull in admit air and supply it to the skin whenever the wearer wishes to initiate cooling. FIG. 3 depicts the use of a "T" or "Y" connector seated in a perforation of the flexible tubing with both of its inlets left open so that when the connector is abutted against the wearer's skin it acts as a spacer of the skin from adjoining perforations in portions of the tubing and thus facilitates evaporation of moisture that may block such perforations. In this embodiment, the open inlets of the "T" or "Y" connector function as lateral outlets for some of the air flowing through the flexible tubing to the skin, thus dissipating moisture seals between the tubing and the skin.

As has been earlier noted herein, the device of this invention can be modified and varied in numerous ways without departing from the scope of this invention. It is accordingly intended that such scope be limited only insofar as the appended claims may require.

What is claimed is:

1. A device for air-cooling the skin of its wearer which comprises:
   (a) a length of flexible tubing adapted to fit around the wearer's torso or another of the wearer's body parts, which tubing contains at least two perforations so situated as to facilitate air cooling of both the front and back of the wearer's torso or another of the wearer's body parts that it is adapted to fit, which length of flexible tubing has both of its ends connected to two separate inlets of
   (b) a connector member selected from among the Y- and T-shaped connectors, each having one additional open inlet, and X-shaped connectors, each having two inlets, one of which has been blocked and one of which is open wherein each additional open inlet is connected to
   (c) a further unperforated length of flexible tubing which, in turn, is connected to
   (d) a hand-operable air aspirator member, which when so hand operated, acts to draw in air and deliver it to each said further unperforated length of tubing, and in turn delivers said air through said connector member into both ends of said first length of tubing from which said air then exits through said at least two perforations and contacts the skin of said wearer.

2. The device of claim 1 in which said hand-operable air aspirator member referred to is part (d) is a sphygmanometer.

3. The device of claim 1 in which said connector is a T-shaped connector.

4. The device of claim 1 in which said connector is a Y-shaped connector.

5. The device of claim 1 in which said flexible tubing is clear vinyl plastic tubing having an outer diameter of about ¼ inch and an inner diameter of about ⅛ inch.

6. The device of claim 1 wherein the tubing of part (a) is provided with at least 4 perforations, positioned to cool the wearer's body part in need thereof, one half of which are positioned to cool one surface of said body part and the other half of which are positioned to cool the opposite surface of said body part.

7. The device of claim 1 wherein the tubing of part (a) has been modified by seating in at least one perforation on each surface of said body part the stem of a very small "T" or "Y"-shaped connector, the twin branched inlets of which each have an inside diameter of not more than about one-half the inner diameter of part (a) itself wherein said branched inlets are left open and allowed to function as outlets for air flowing through said tubing of part (a) so that when abutted to the wearer's skin, they act to space adjoining portions of part (a) away from the wearer's skin and thereby (i) to eliminate adherence of said portions of part (a) to the skin, (ii) to break any moisture seal caused by such adherence and (iii) to dissipate said moisture rapidly.

* * * * *